(12) United States Patent
Wellings

(10) Patent No.: US 10,471,130 B2
(45) Date of Patent: Nov. 12, 2019

(54) MICROPARTICLES

(71) Applicant: Spheritech Ltd., Runcorn, Cheshire (GB)

(72) Inventor: Donald A. Wellings, Runcorn (GB)

(73) Assignee: Spheritech Ltd., Runcorn, Cheshire (GB)

( * ) Notice: Subject to any disclaimer, the term of this patent is extended or adjusted under 35 U.S.C. 154(b) by 0 days.

(21) Appl. No.: 16/330,184

(22) PCT Filed: Sep. 5, 2017

(86) PCT No.: PCT/EP2017/072270
§ 371 (c)(1),
(2) Date: Mar. 4, 2019

(87) PCT Pub. No.: WO2018/042059
PCT Pub. Date: Mar. 8, 2018

(65) Prior Publication Data
US 2019/0201497 A1    Jul. 4, 2019

(30) Foreign Application Priority Data

Sep. 5, 2016  (GB) .................................. 1615050.0

(51) Int. Cl.
| | |
|---|---|
| *A61K 38/42* | (2006.01) |
| *A61K 47/18* | (2017.01) |
| *A61K 47/12* | (2006.01) |
| *A61K 9/50* | (2006.01) |
| *A61K 47/22* | (2006.01) |

(52) U.S. Cl.
CPC ............ *A61K 38/42* (2013.01); *A61K 9/5021* (2013.01); *A61K 47/12* (2013.01); *A61K 47/18* (2013.01); *A61K 47/22* (2013.01)

(58) Field of Classification Search
CPC ........ A61K 38/42; A61K 47/18; A61K 47/12; A61K 9/5021; A61K 47/22
See application file for complete search history.

(56) References Cited

FOREIGN PATENT DOCUMENTS

| | | | | |
|---|---|---|---|---|
| EP | 2014280 A1 | 1/2009 | | |
| WO | WO2012/143508 | * 10/2012 | ............ | C08G 69/48 |
| WO | WO 2012/143508 A1 | 10/2012 | | |
| WO | WO 2014/179793 A1 | 11/2014 | | |

OTHER PUBLICATIONS

International Search Report and Written Opinion, counterpart International Appl. No. PCT/EP2017/072270 dated Nov. 7, 2017, (8 pages).

(Continued)

*Primary Examiner* — Trevor Love
(74) *Attorney, Agent, or Firm* — Cook Alex Ltd.

(57) ABSTRACT

The invention provides a blood substitute product comprising haemoglobin and a self-assembled microparticle having an acid having two or more acid groups and an organic base in a solvent. The particle is of micron scale. The microparticle may be obtained by contacting a bis-acid and organic base in a hydrophilic solvent, wherein the acid is insoluble or sparingly soluble in the hydrophilic solvent and the organic base is soluble in a hydrophilic solvent.

7 Claims, 3 Drawing Sheets

Brassylic acid microspheres (not cross-linked)

(56) References Cited

OTHER PUBLICATIONS

Rameez, Shahid et al., "Biocompatible and Biodegradable Polymersome Encapsulated Hemoglobin: A Potential Oxygen Carrier", Bioconjugate Chemistry, vol. 19, No. 5, pp. 1025-1032 (May 1, 2008).
Jabbari, Esmaiel, "Targeted Delivery with Peptidomimetic Conjugated Self-Assembled Nanoparticles", Pharmaceutical Research, vol. 26, No. 3, pp. 612-630 (Mar. 2009).
Xiong, Yu et al., Hemoglobin-Based Oxygen Carrier Microparticles: Synthesis, Properties, and In Vitro and In Vivo Investigations, Biomacromolecules, vol. 13, No. 10, pp. 3292-3300 (Oct. 8, 2012).
Arifin and Palmer, "Polymersome Encapsulated Hemoglobin: A Novel Type of Oxygen Carrier", Biomacromolecules, vol. 6, pp. 2172-2182, 2005.
Chen, et al., "Low Modulus Biomimetic Microgel Particles with High Loading of Hemoglobin", Biomacromolecules, vol. 13, pp. 2748-2759, 2012.
Li, et al, "Asymmetric Copolymer Vesicles to Serve as a Hemoglobin Vector forf Ischemia Therapy", Biomaterials Science, vol. 2, pp. 1254-1261, 2014.
UK Search Report dated Apr. 28, 2017 for GB Application No. GB1615050.0.
UK Search Report dated May 17, 2018 for GB Application No. GB1714257.1.

* cited by examiner

Figure 1 – Brassylic acid microspheres (not cross-linked)
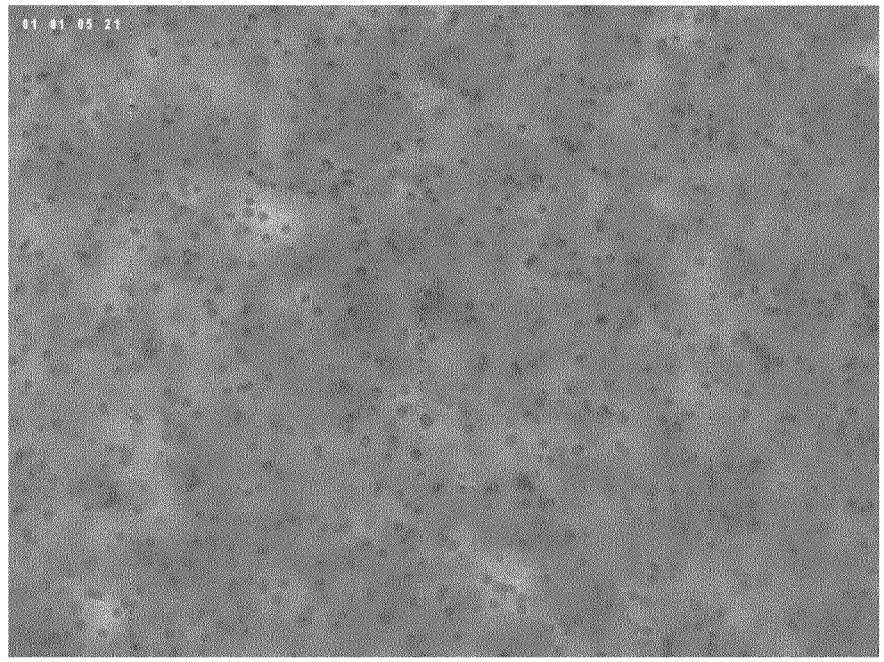
Figure 2 – Brassylic acid-PDAC microspheres (not cross-linked)
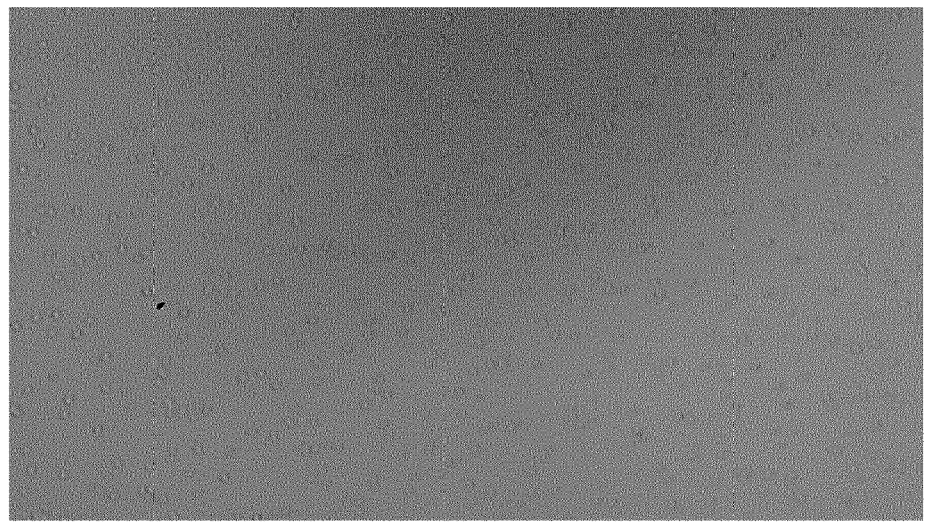

Figure 3 – Scanning electron micrograph of cross-linked haemoglobin microspheres
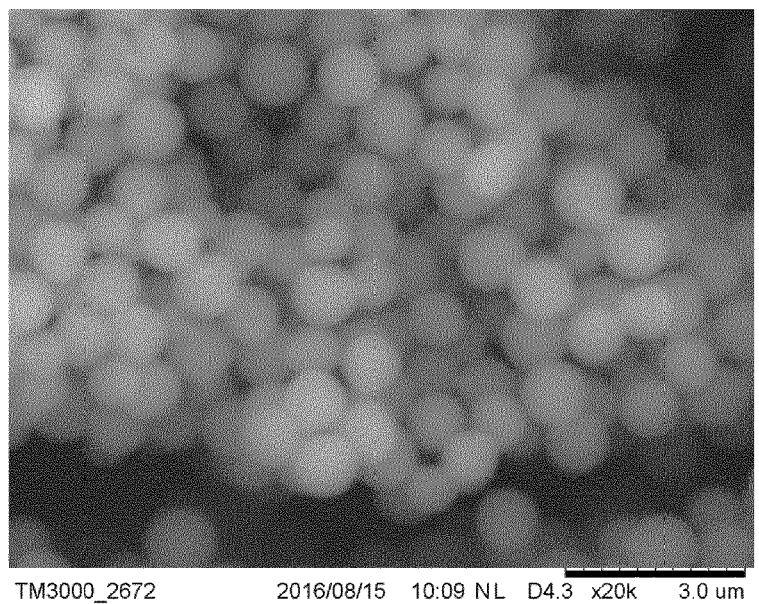
Figure 4 – Microscope photograph of cross-linked haemoglobin microspheres from example 7
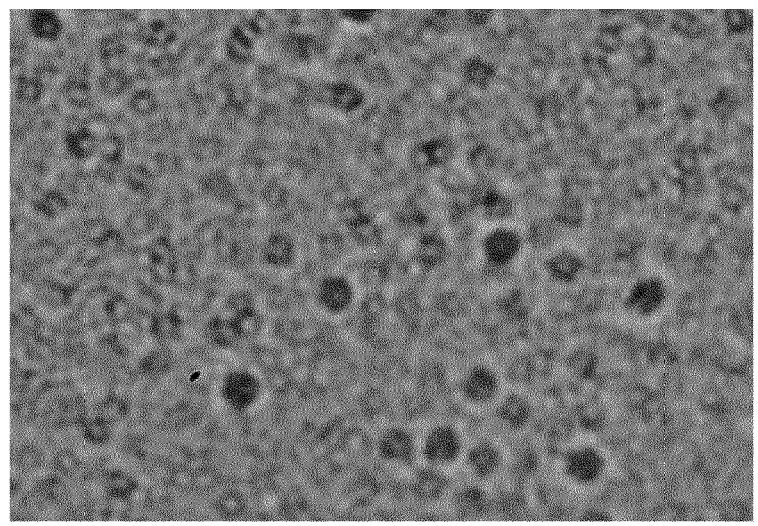

Figure 5 – Microscope photograph of cross-linked haemoglobin microspheres from example 8
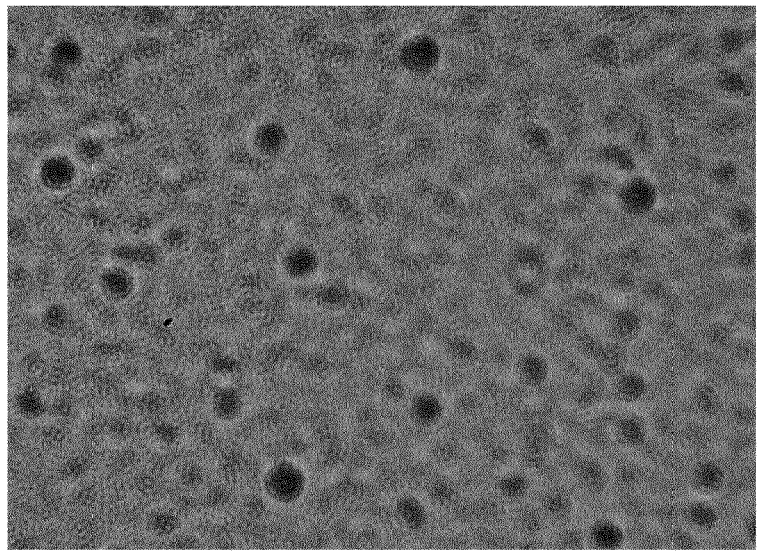

MICROPARTICLES

This invention relates to a microparticles, in particular to self-assembled microparticles and their use as a component of an artificial blood product or a blood substitute and a method of preparing the microparticles. The microparticles and porous materials are useful in a wide range of physical and chemical processes especially where circulation in the blood stream is required.

Blood surrogates, also referred to as artificial blood, blood substitutes or oxygen carrying substitutes are of immense importance in circumstances where immediate blood supply is required but cannot be supplied through traditional blood transfusion. This can be for example in cases of haemophilia, in trauma units, in cases where blood can be contaminated by disease, during transplant surgery, or in remote locations away from medical facilities, for example on the battlefield and in road traffic accidents. A major purpose behind blood substitutes is the elimination of immune response, often seen in donor blood, and elimination of disease transmission. Religious objection to blood transfusion is also a limiting factor with donated blood. Blood substitutes can also be used for the storage and preservation of donor organs and other body tissues.

It is also essential that the manufacturing process and cost of the ultimate substitute is cost effective. A 60 g unit of donor blood typically costs a hospital $300 therefore the price of a blood substitute would need to be less than $5 per gram or provide a compelling reason for use.

Investigation into development of viable blood substitutes has been ongoing for more than 70 years. The primary driver, the transport of oxygen by red blood cells has steered most research into the development of haemoglobin-based oxygen carriers (HBOCs).

The chemical carrier of oxygen in haemoglobin is protoporphyrin IX which has more recently stimulated additional research into porphyrin based technologies.

Microparticles as blood substitutes are known, for example as described in WO9629346, WO2006108047 U.S. Pat. No. 6,498,141, HK1207560, U.S. Pat. Nos. 5,770,727 5,387,672.

Known blood substitutes suffer from a number of disadvantages. Some side effects reported include transient yellow skin discoloration, nausea, mild to moderate increase in blood pressure (10 to 20 mm/Hg), vomiting, low urine output, difficulty swallowing, flatulence, and low red blood cell count. Existing methodology for preparation of HBOCs suffers from complex manufacturing processes and result in polymers with broad ranges in size or heterogeneous polymeric forms of haemoglobin. The processes for manufacture often include complex organic chemistry, laborious dialysis and/or chromatographic separation technologies which are difficult to scale up. The current HBOCs in trials or development are often cross-linked with cytotoxic chemicals including, for example aldehydes such as glutaraldehyde where the mechanism of crosslinking is well known to be random, ill-defined and difficult to reproduce. It is postulated that dimeric forms of haemoglobin may be the cause of toxic effects in some HBOCs, however, the methods of crosslinking described in other HBOCs could be responsible for toxicity.

It is known that haemoglobin can be cross-linked with bis-carboxy fatty acids. However known cross-linked haemoglobins disadvantageously have a broad molecular weight range and require complex and laborious purification processes including gel permeation, anion exchange and cation exchange chromatography to provide a usable product.

We have now found that these and other problems associated with known blood substitute products may be ameliorated by providing a particulate support comprising a self-assembled microparticle comprising a fatty acid having two or more carboxylic acid groups and a base which provide a narrow particle size distribution or macroporous material formed by contacting self-assembled microparticles. The microparticles are suitably biodegradable.

In a first aspect, the invention provides a blood substitute composition comprising mammalian haemoglobin and a self-assembled microparticle. Suitably the microparticle comprises an acid having two or more acid groups and an organic base which is soluble in a hydrophilic solvent.

Suitably, the blood substitute composition comprises a stable polymerized haemoglobin solution, comprising mammalian hemoglobin cross-linked with a self-assembled microparticle.

The term "blood-substitute" as employed herein denotes a HBOC composition for use in humans, mammals and other vertebrates. The HBOC is capable of transporting and transferring oxygen to vital organs and tissues. A vertebrate is defined to include humans, or any other vertebrate animals which uses blood in a circulatory system to transfer oxygen to tissue. By way of examples a preferred vertebrate for treatment with the substance of this invention is a mammal, such as a primate, a canine, a feline, an equine, a porcine, a bovine, an ovine, a rodent or an avian. A vertebrate treated with the substance of this invention can be fetal, post-natal vertebrate, or a vertebrate at time of birth. The HBOC substance described herein may also be used for the storage and preservation of donor organs and mammalian tissues.

The use of a self-assembled microparticle enables a polymer of haemoglobin, of a regular size and shape and narrow molecular weight distribution to be produced. The microparticle contains natural materials, which are cross-linked by amide bonds and are therefore biodegradable by protease activity. As such, they are likely to be of little, or no concern to physiological functions. The present microparticles are advantageously monodispersed and small enough to travel through the smallest of capillaries where oxygen transfer occurs.

The weight to weight ratio of the haemoglobin to cross-linking agent are significantly lower than hitherto known. Known products have a molecular weight in the range of $1.7 \times 10^7$.

The present invention provides microparticles having a molecular weight of at least $1.0 \times 10^8$, preferably from $1.6 \times 10^{11}$ to $2 \times 10^{13}$ for example $4 \times 10^{12}$.

Haemoglobin from any suitable source may be used to prepare the blood substitute of the present invention. Examples include old or outdated human blood, bovine blood, ovine blood, porcine blood, equine blood, and blood from other vertebrates. Transgenic haemoglobin, such as the transgenic haemoglobin described in EIO/TECHNOLOGY, 1z: 55-59 (1994) and recombinant haemoglobin (Nature, 356:258-60 (1992)) can also be used.

The microparticle acid suitably comprises a bis-acid, preferably a bis-aliphatic acid and suitably comprises two or more carboxylic acid groups, although other acid groups may be employed. Suitably the bis-acid is insoluble or sparingly soluble in the hydrophilic solvent. Suitably, by contacting the acid, preferably bis-aliphatic acid with an organic base which is soluble in the hydrophilic solvent, the acid may be solubilised.

The solvent is suitably hydrophilic, preferably an aqueous solution, for example a water in oil emulsion within an aqueous phase, and especially water. Advantageously, an aqueous-based solvent, preferably water, allows the microparticle to be used in applications in which environmental considerations are important. For example, the microparticle may be formulated into an aqueous-based product which may be suitable for personal use or consumption, medical uses and for example as a biocide.

In the preferred embodiment the bis-aliphatic acid comprises a bis-carboxylic fatty acid in which terminal carboxylic acids are linked by a region which is less hydrophilic than the terminal carboxylic acids and is preferably hydrophobic. The less hydrophilic region may comprise a backbone with substituents and/or the backbone may comprise heteroatoms, for example poly-epsilon lysine. Preferably the region linking the carboxylic acids is hydrophobic and preferably a hydrocarbyl group. In an especially preferred embodiment, the hydrophobic group is an aliphatic hydrocarbyl group. Preferably, the bis-acid comprises a compound of general formula $HOOC-(CH_2)_n-COOH$ wherein n is sufficiently large that the bis acid is sparingly soluble or insoluble in water. Preferably n is at least 5, more preferably at least 6, especially at least 7. Suitably n is not more than 40, preferably not more than 36, more preferably not more than 25, and especially not more than 20. Preferably n is from 7 to 18.

In a preferred embodiment, the organic acid comprises a $C_7$ to $C_{18}$ bis carboxylic fatty acid. In another preferred embodiment, the organic acid comprises a $C_7$ to $C_{13}$ bis carboxylic fatty acid together with a further acid selected from a EDTA, nitrolotriacetic acid and a monocarboxylic acid, preferably a $C_6$ to $C_{18}$ carboxylic acid, for example caproic acid, palmitic acid and octanoic acid.

By selecting more than one acid for example in which the acids have different n values, the size of the microparticle may be tailored. A longer hydrophobic portion connecting the acid groups suitably provides a larger microparticle. For example where n is 8, sebacic acid, a particle of size 2.6 microns may be obtained and where n is 11, brassylic acid, a particle of size 3.0 microns may be obtained.

The bis-carboxy fatty acid can also be unsaturated for example traumatic acid, or substituted or both unsaturated and substituted. Suitably, the substitution does not cause the bis-acid to be soluble in aqueous solution. When the bis-aliphatic acid is contacted with the aid of a solvent soluble organic base, microparticles are formed spontaneously.

The bis-aliphatic acid may comprise: a bis-phosphonic acid of general formula $(HO)_2OP-(CH_2)_n-PO(OH)_2$ or an unsaturated bis-phosphonic acid; a mono-carboxylic mono-phosphonic acid of general formula $HOOC-(CH_2)_n-PO(OH)_2$ or an unsaturated version of such bis-acid; a bis-sulfonic acid of general formula $(HO)O_2S-(CH_2)_n-SO_2(OH)$ or an unsaturated version of such bis-acid; a mono-carboxylic mono-sulfonic acid of general formula $HOOC-(CH_2)_n-SO_2(OH)$ or an unsaturated version of such a bis-acid; a bis-boronic acid of general formula $(HO)_2B-(CH_2)_n-B(OH)_2$ or an unsaturated bis-boronic acid, or substituted bis-boronic acid; a mono-carboxylic mono-boronic acid of general formula $HOOC-(CH_2)_n-B(OH)_2$ an unsaturated version of such bis-acid; or a substituted version of said bis-acids. In these acids, n is sufficiently large that the bis acid is sparingly soluble or insoluble in water. Preferably n is at least 5, more preferably at least 6 and especially at least 7. Suitably n is not more than 40, preferably not more than 36 more preferably not more than 25, and especially not more than 20. Preferably n is from 7 to 18.

Suitably, the organic base combines with the bis-acid moieties such that the combination of the two components comprises two separate hydrophilic or ionic head regions connected by a hydrophobic region. Without wishing to be bound by theory, it is believed that the hydrophobic regions and hydrophilic regions of adjacent bis-acids with organic base align to form micelles and lead to self-assembly of the microparticles of the invention. Preferably, the microparticle comprises a multi-lamellar structure in which further molecules comprising the bis-acids with the organic base, align with the hydrophilic head of another bis-acid/organic base so as to form a multi-lamellar structure.

The organic base may be selected from a range of bases which, together with the bis-acid forms a self-assembling microparticle. Preferably, the organic base comprises an amine, suitably an aliphatic amine or an aromatic amine having a basic character or other nitrogen-containing base. Examples of suitable organic bases include alkylated amines and polyamines including amines having one or two $C_{1-4}$ N-alkyl-groups, for example methylated amines. Examples of preferred amines include N-methylmorpholine, 4-methylmorpholine (NMM), N,N-dimethylaminoethanol (DMAE), 4-dimethylaminopyridine (DMAP), imidazole or 1-methylamidazole, poly(diallyldimethylammonium chloride) (PDAC), didecyldimethylammonium chloride (DDAC) and dodecyldipropylenetriamine (DDPT).

In preferred embodiments, the acid is suitably one or more of brassylic acid, sebacic acid and azelaic acid in combination with a base selected from methylmorpholine (NMM), N,N-dimethylaminoethanol (DMAE), 4-dimethylaminopyridine (DMAP), imidazole, 1-methylamidazole, poly(diallyldimethylammonium chloride) (PDAC), didecyldimethylammonium chloride (DDAC) and dodecyldipropylenetriamine (DDPT).

Preferred examples include microparticles comprising brassylic acid and PDAC, brassylic acid and DDAC, brassylic acid and DDPT, sebacic acid and NMM, poly epsilon lysine in combination with one or more of sebacic acid, brassylic acid and azelaic acid.

We have found that microparticles according to the invention comprising amines having antimicrobial properties are particularly suited for use as antimicrobial compositions and biocides. The level of antimicrobial activity of the base may be higher when in the form of a self-assembled microparticle according to the invention as compared to when in a conventional formulation.

According to a further aspect the invention also provides the use of a self-assembled microparticle comprising a bis acid and a water-soluble base, the base being displaceable by a protein and for covalent cross-linking.

In a further aspect, the invention provides a self-assembled microparticle comprising an acid having two or more acid groups, preferably a bis acid, covalently bonded to a haemoglobin molecule.

The covalently bonded haemoglobin is suitably produced by adding haemoglobin to a self-assembled microparticle comprising an acid having two or more acid groups and a water-soluble base which is displaceable in part or whole by haemoglobin.

The protein suitably comprises haemoglobin either individually or in combination with one or more other proteins, for example a catalase and a superoxide dismutase.

The acid and base are suitably combined in relative quantities such that the molar ratio of acid groups in the acid to basic groups in the base is approximately stoichiometric such that self-assembled microparticles form. The molar quantity of acid groups to base groups may be less or more than stoichiometric provided the self-assembled particles form. Where the ratio of acid groups to base groups is too low or too high, —assembled particles do not form as the excess component disrupts structure of the acid and base. The ratio of acid groups to basic groups that allow formation of the self-assembled particle will vary depending on the particular acid and particular base.

The skilled person will be able to determine whether a self-assembled particle is formed by observing under a microscope with magnification at a level to visually observe particles for example at 40× magnification. The relative quantities of the acid and base will be able to be modified to determine the minimum and maximum ratio of the components at which microparticles form. Acids having longer chains may provide microparticles which are more stable than microparticles (with the same base and same molar ratio) comprising an acid having a shorter chain. The greater stability may allow a lower level of acid to be employed and a lower ratio of acid groups to basic groups may still allow a microparticle to form.

Suitably, the ratio of acid groups to basic groups in the acid and base is from 0.6 to 1.4:1, preferably 0.7 to 1.3:1, more preferably 0.8 to 1.2:1 and desirably 0.9 to 1.1:1. Sebacic acid and brassylic acid are examples of preferred acids. Suitably a microparticle comprising sebacic acid with a base has a ratio of sebacic acid to base of 0.85 to 1.15:1. A microparticle comprising brassylic acid with a base has a ratio of brassylic acid to base of 0.8 to 1.2:1. In a preferred embodiment, the acid and base are present at levels to provide a molar ratio of acid groups to basic groups of 1:1.

The organic base may be reactive so as to enable cross-linking of the self-assembled microparticles for form a macroporous material. The organic base need not be reactive in which case it may suitably be displaced by another reactive species to allow subsequent cross-linking to form a macroporous material. The solvent soluble organic base can be displaced by addition of a reactive species including, but not limited to, amine containing organic components. The amine suitably allows cross-linking of the microparticles by amide bond formation. In the preferred embodiment the amine containing organic component is a polymeric amine including but not limited to a peptide, protein, polyallylamine, polyethyleneimine and other polyamines.

Examples of suitable amines and polyamines include ethylenediamine, poly-e-lysine, polyallylamine, polyethyleneimine, aminopropyltrialkoxysilanes, 3-(2-aminoethylamino)propyltrimethoxysilane, N-(3-(trimethoxysilyl)-propyl)diethyenetriamine.

In formation of the microparticle or macroporous material the above aforementioned bis acids may be mixed in any proportions. In addition, the reactive amines may also be mixed.

Suitably, the microparticles comprise functional components, tailored according to the intended use.

A self-assembled microparticle or macroporous material according to the invention may also comprise a functional material supported by the polymer. Examples of suitable functional materials include a catalyst, an initiator species for peptide synthesis or oligonucleotide synthesis, a pharmaceutical active, an agrochemical active, a macromolecule, an enzyme, a nucleic acid sequence and a protein.

The invention is particularly useful in supporting precious metal catalysts, for example palladium catalysts. A particular advantageous example is palladium.

The self-assembled microparticle may be produced by a method comprising contacting the acid having two or more acid groups with an organic base in an aqueous medium, preferably water.

Suitably the polymerisation and cross-linking is initiated by processes known to those skilled in the art. For example, self-assembled microparticles prepared in water with an amine containing component can be cross-linked using a water soluble carbodiimide.

Suitably, the self-assembled microparticle material according to the invention is substantially mono-disperse. That is the material has particles which are all substantially the same size. Monodisperse microparticles may advantageously travel in the blood stream without transferring across capillary walls or blocking capillaries, effectively behaving in a similar manner to an erythrocyte.

The self-assembled microparticles of the present invention may be used in separate or combined processes, for example, drug delivery in combination with oxygen transport.

The self-assembled microparticles may be used as a carrier to carry a compound which is to be released over a period of time, for example a pharmaceutical. This use provides a means of tailoring a dosage regime of the compound according to the loading of the compound in the support. In the case of a pharmaceutical, this may be advantageous in assisting the correct dosage of an active, for example with continuous slow release rather than requiring a patient to take periodic large doses.

The microparticles of the invention may be formulated into a composition for a wide-range of variations in use, including a composition containing haemoglobin in combination with other proteins or enzymes such as a catalase, or in combination with compounds that provide and allosteric effect such as 2,3-bisphosphoglyceric acid The invention is illustrated by the following non-limiting examples.

Example 1—Preparation of Self-Assembled Microparticles

Brassylic acid (1.54 g, 6.31 mmol) and 4-dimethylaminopyridine (DMAP, 1.54 g, 12.62 mmol) were dissolved in water (10 cm$^3$) and a sample placed on a microscope. Almost monodispersed spherical entities of ~3 µm diameter were observed (FIG. 1).

Example 2—Preparation of Self-Assembled Microparticles

Brassylic acid (1.54 g, 6.31 mmol) and dimethylaminoethanol (DMAE, 1.12 g, 12.62 mmol) were dissolved in water (10 cm$^3$) and a sample placed on a microscope. Almost monodispersed spherical entities of ~3 µm diameter were observed.

Example 3—Preparation of Self-Assembled Microparticles

Brassylic acid (1.54 g, 6.31 mmol) and 4-methylmorpholine (NMM, 1.275 g, 12.62 mmol) were dissolved in water (10 cm$^3$) and a sample placed on a microscope. Almost monodispersed spherical entities of ~3 µm diameter were observed.

Example 4—Preparation of Self-Assembled Microparticles

The above dicarboxylic acid dissolution experiments were also carried out using a range of acids and a range of water soluble organic bases. Some of the combinations tested are listed below. The combinations had an acid group to basic group molar ratio of 0.9 to 1.1:1. All of these combinations formed the spherical entities as described in Example 1.

Pimelic acid plus NMM
Suberic acid plus NMM
Azelaic acid plus NMM
Sebacic acid plus NMM
Sebacic acid plus DMAP
Sebacic acid plus DMAE
Sebacic acid plus imidazole
Dodecanedioic acid plus NMM
Dodecanedioic acid plus DMAP
Dodecanedioic acid plus DMAE
C36 dimer acid plus NMM

Example 5—Poly(Diallyldimethylammonium Chloride) (PDAC) SpheriSomes

PDAC (1.615 g, 10 mmol) was dissolved in water (50 cm$^3$) and NaOH (0.4 g, 10 mmol) added. Brassylic acid (1.22 g, 5 mmol) was added to this solution and allowed to dissolve overnight. This appeared by visual inspection to be a clear solution but was confirmed to be a suspension of ~3 μm microparticles when observed under the microscope. A microscope photograph is shown in FIG. 2.

Example 6—Preparation of Cross-Linked Self-Assembled Microparticles Containing Haemoglobin PDAC (16.167 g of 20% solution, 20 mmol) was dissolved in water (100 cm$^3$) and NaOH (0.8 g, 20 mmol) added. Brassylic acid (2.44 g, 10 mmol) was added to this solution and allowed to dissolve. Human haemoglobin (2.44 g) was dissolved in water (100 cm$^3$) and added to the solution of brassylic acid/PDAC SpheriSomes. The mixture was filtered through a 0.5 μm cartridge and a sample placed on a microscope. Microspheres of ~3 μm diameter were still present. A solution of N-(3-Dimethylaminopropyl)N'-ethyl-carbodiimide hydrochloride (EDCl)(4.6 g, 24 mmol) and 1-hydroxybenzotriazole (HOBt) (0.47 g, 1.2 mmol) were dissolved in water (50 cm$^3$) and added to the above solution. The cross-linking reaction was left overnight, the resultant particles washed by tangential flow filtration (TFF). It was noted that the supernatant was colourless confirming that the haemoglobin was incorporated into the SpheriSomes. A sample of the SpheriSomes was lyophilised. FIG. 3 shows a scanning electron micrograph of the resultant microspheres.

Example 7—Preparation of Cross-Linked Self-Assembled Microparticles Containing Haemoglobin PDAC (16.167 g of 20% solution, 20 mmol) was dissolved in water (100 cm$^3$) and NaOH (0.8 g, 20 mmol) added. Brassylic acid (2.44 g, 10 mmol) was added to this solution and allowed to dissolve. Human haemoglobin (3.66 g) was dissolved in water (100 cm$^3$) and added to the solution of brassylic acid/PDAC SpheriSomes. The mixture was filtered through a 0.5 μm cartridge and a sample placed on a microscope. Microspheres of ~3 μm diameter were still present. A solution of EDCl (4.6 g, 24 mmol) and HOBt (0.47 g, 1.2 mmol) were dissolved in water (50 cm$^3$) and added to the above solution. The cross-linking reaction was left overnight, the resultant particles washed by tangential flow filtration (TFF). It was noted that the supernatant was colourless confirming that the haemoglobin was incorporated into the SpheriSomes. FIG. 4 shows a microscope photograph of the resultant microspheres.

Example 8—Preparation of Cross-Linked Self-Assembled Microparticles Containing Haemoglobin PDAC (16.167 g of 20% solution, 20 mmol) was dissolved in water (100 cm$^3$) and NaOH (0.8 g, 20 mmol) added. Brassylic acid (2.44 g, 10 mmol) was added to this solution and allowed to dissolve. Human haemoglobin (4.88 g) was dissolved in water (100 cm$^3$) and added to the solution of brassylic acid/PDAC SpheriSomes. The mixture was filtered through a 0.5 μm cartridge and a sample placed on a microscope. Microspheres of ~3 μm diameter were still present. A solution of EDCl (4.6 g, 24 mmol) and HOBt (0.47 g, 1.2 mmol) were dissolved in water (50 cm$^3$) and added to the above solution. The cross-linking reaction was left overnight, the resultant particles washed by tangential flow filtration (TFF). It was noted that the supernatant was slightly pink confirming the majority of the haemoglobin was incorporated into the SpheriSomes. FIG. 5 shows a microscope photograph of the resultant microspheres.

Example 9—Preparation of Cross-Linked Self-Assembled Microparticles Containing Haemoglobin L-Carnitine (1.612 g, 10 mmol) was suspended in water (20 cm$^3$) and NaOH (0.4 g, 10 mmol) added. Brassylic acid (1.22 g, 5 mmol) was added to this solution and the mixture allowed to dissolve. Human haemoglobin (1.83 g) was dissolved in water (200 cm$^3$) and added to the solution of Brassylic acid/carnitine SpheriSomes. The mixture was filtered through a 0.5 μm cartridge and a sample placed on a microscope. Microspheres of ~3 μm diameter were present. A solution of EDCl (4.6 g, 24 mmol) and HOBt (0.37 g, 2.4 mmol) were dissolved in water (25 cm$^3$) and added to the above solution. The cross-linking reaction was left overnight, the resultant particles washed by tangential flow filtration (TFF). It was noted that the supernatant was colourless confirming that the haemoglobin was incorporated into the SpheriSomes.

Example 10—Preparation of Cross-Linked Self-Assembled Microparticles Containing Haemoglobin Tetraethyl ammonium hydroxide (TEA.OH) (4.2 cm$^3$ of a 35% solution, 10 mmol) was added to water (20 cm$^3$) and Brassylic acid (1.22 g, 5 mmol) was added to this solution. The Brassylic acid dissolved immediately to form SpheriSomes. Human haemoglobin (1.83 g) was dissolved in water (200 cm$^3$) and added to the solution of Brassylic acid/TEA.OH SpheriSomes. The mixture was filtered through a 0.5 μm cartridge and a sample placed on a microscope. Microspheres of ~3 μm diameter were still present. A solution of EDCl (2.3 g, 12 mmol) and HOBt (0.18 g, 1.2 mmol) were dissolved in water (25 cm$^3$) and added to the above solution. The cross-linking reaction was left overnight, the resultant particles washed by tangential flow filtration (TFF). It was noted that the supernatant was colourless confirming that the haemoglobin was incorporated into the SpheriSomes.

The invention claimed is:

1. A blood substitute product comprising mammalian haemoglobin and a self-assembled microparticle in which the microparticle comprises an acid having two or more acid groups and an organic base which is soluble in a hydrophilic solvent;

wherein the acid comprises brassylic acid, sebacic acid, and/or azelaic acid;

wherein the organic base comprises one or more of N-methylmorpholine, N,N-dimethylaminoethanol, 4-dimethylaminopyridine, imidazole, 1-methylamidazole, poly(diallyldimethylammonium chloride) (PDAC), didecyldimethylammonium chloride (DDAC), dodecyldipropylenetriamine (DDPT) and poly epsilon lysine.

2. A blood substitute product according to claim 1 in which the blood substitute product comprises a stable polymerized haemoglobin solution, comprising mammalian haemoglobin cross-linked with a self-assembled microparticle.

3. A blood substitute product according to claim 1 in which the microparticle has a particle size of 0.5 to 10 microns.

4. A blood substitute product according to claim 1 in which the molar ratio of acid groups to basic groups in the acid and base is from 0.6 to 1.4:1.

5. A blood substitute product according to claim 1 in which the molar ratio of acid groups to basic groups is from 0.7 to 1.3:1.

6. A blood substitute product according to claim 1 in which the microparticle comprises a multi-lamellar structure.

7. A blood substitute product according to claim 1 in which the acid is reacted with haemoglobin to form a cross-linked species.

* * * * *